United States Patent
Takada

(10) Patent No.: US 9,951,308 B2
(45) Date of Patent: Apr. 24, 2018

(54) TEMPERATURE-RESPONSIVE CELL CULTURE SUBSTRATE AND METHOD FOR PRODUCING SAME

(71) Applicant: DIC Corporation, Tokyo (JP)

(72) Inventor: Tetsuo Takada, Sakura (JP)

(73) Assignee: DIC Corporation, Tokyo (JP)

( * ) Notice: Subject to any disclaimer, the term of this patent is extended or adjusted under 35 U.S.C. 154(b) by 123 days.

(21) Appl. No.: 15/106,470

(22) PCT Filed: Dec. 11, 2014

(86) PCT No.: PCT/JP2014/082861
§ 371 (c)(1),
(2) Date: Jun. 20, 2016

(87) PCT Pub. No.: WO2015/093393
PCT Pub. Date: Jun. 25, 2015

(65) Prior Publication Data
US 2017/0029763 A1 Feb. 2, 2017

(30) Foreign Application Priority Data

Dec. 20, 2013 (JP) ................. 2013-263815

(51) Int. Cl.
| | |
|---|---|
| *C12N 5/07* | (2010.01) |
| *C12N 5/00* | (2006.01) |
| *C12M 1/12* | (2006.01) |
| *C08L 33/14* | (2006.01) |
| *C08L 33/24* | (2006.01) |
| *C08L 39/04* | (2006.01) |
| *C08L 39/06* | (2006.01) |

(52) U.S. Cl.
CPC ............ *C12N 5/0068* (2013.01); *C08L 33/14* (2013.01); *C08L 33/24* (2013.01); *C08L 39/04* (2013.01); *C08L 39/06* (2013.01); *C12M 25/02* (2013.01); *C12M 25/14* (2013.01); *C12N 2533/30* (2013.01); *C12N 2539/10* (2013.01)

(58) Field of Classification Search
CPC .................................................... C12N 5/0068
See application file for complete search history.

(56) References Cited

U.S. PATENT DOCUMENTS

| | | |
|---|---|---|
| 5,284,766 A | 2/1994 | Okano et al. |
| 2011/0097802 A1 | 4/2011 | Takada et al. |
| 2014/0235748 A1 | 8/2014 | Haraguchi et al. |

FOREIGN PATENT DOCUMENTS

| | | |
|---|---|---|
| JP | 05-192130 A | 8/1993 |
| JP | 05-192138 A | 8/1993 |
| JP | 06-104061 B2 | 12/1994 |
| JP | 4430123 B1 | 3/2010 |
| JP | 2013-057058 A | 3/2013 |

OTHER PUBLICATIONS

International Search Report and Written Opinion dated Mar. 17, 2015, issued for PCT/JP2014/082861.

*Primary Examiner* — Arrie L Reuther
(74) *Attorney, Agent, or Firm* — Locke Lord LLP

(57) ABSTRACT

Provided is a cell culture substrate, in which polymer (B) having a lower critical solution temperature contained in the substrate is a copolymer of a monomer (a) that becomes a hydrophobic polymer in homopolymerization and a monomer (b, c or d) that becomes a hydrophilic polymer in homopolymerization, which is uncrosslinked, and the lower critical solution temperature of the obtained copolymer (B) can be controlled widely by the types and ratio of the two monomers, to easily detach the cultured cells from the culture substrate surface rapidly without using protein hydrolase and collect the cells without damage. This cell culture substrate contains a polymer (A) of a (meth)acrylic acid ester monomer (a), one or more types of inorganic materials (C) selected from a water-swellable clay mineral and silica, and a polymer (B) having a lower critical solution temperature and including a monomer (a) and a monomer (b, c or d).

8 Claims, No Drawings

TEMPERATURE-RESPONSIVE CELL CULTURE SUBSTRATE AND METHOD FOR PRODUCING SAME

TECHNICAL FIELD

The present invention relates to a technique of cell culture, and specifically relates to a cell culture substrate which is capable of easily detaching and collecting cultured cells only by a temperature change, without using chemicals such as trypsin, and a method for producing the same.

BACKGROUND ART

In the related art, as a cell culture substrate such as an animal tissue, a plastic (for example, polystyrene) container has been widely used. In order that the plastic container allows the cell culture to be effectively performed, a surface thereof is subjected to a plasma treatment or a surface treatment which is performed through the coating by using silicon or a cell attachment factor. In a case where such a cell culture container is used as the culture substrate, the cultured (proliferated) cells are attached on the surface of the container, and in order to detach and collect the cells, it is necessary to separate the cells from the surface of the container by using protein hydrolase such as trypsin or chemicals. An operation of separating the cells by using such enzyme and chemicals is a complicated step, and it is likely that impurities such as bacteria, DNA, and RNA are mixed. In addition, not only a bonding part between the cells and substrate is debonded, but also the bonding between the cells is debonded. For this reason, there is a problem in that the cells in a state of being proliferated (for example, a sheet state) cannot be extracted or are damaged, which causes the change of the cell properties.

In recent years, a technique in which the surface of the cell culture container is very thinly coated with a polymer having a lower critical solution temperature, such as poly-N-isopropyl acrylamide, the polymer exhibits the hydrophobicity at the cell culture temperature, the cells are attached to the polymer, after the cells are cultured, the adhesiveness between the cells and the polymer is decreased by subjecting the polymer to a low temperature treatment, and then the cells are separated in a sheet state from the substrate without using the hydrolytic enzyme and the chemicals was reported (for example, refer to PTL 1 and PTL 2).

However, a polymer such as poly-N-isopropyl acrylamide has low adhesiveness to a surface of plastic such as polystyrene, and when contacting with water, a coated polymer layer is easily detached. Thus, it is necessary to fix the polymer so as not to detach such a polymer layer from the surface of the plastic even in a case of contact with water. As one method for fixing the polymer, there is a method for allowing the surface of the cell culture substrate to be coated with a solution of N-isopropyl acrylamide (monomer) and then performing graft polymerization by irradiation of electron beams (for example, refer to PTL 3).

With respect to the graft polymerization by irradiation of electron beams, the cross-linking reaction between the polymers is necessarily caused on the polymerization, and with the progress of the degree of crosslinking, a temperature response rate of the polymer is greatly decreased, thereby causing a problem that a long period of time for maintaining a low temperature is required in order to make the polymer hydrophilic, and a problem that the cells are damaged during that time since they are also exposed at a low temperature for a long period of time. In addition, when the cell culture substrate produced by using the method is subjected to a sterilization treatment with radiation (for example, γ line), the temperature responsivity of the polymer becomes greatly decreased, which causes a problem that the original ability with which the cells are apt to detach therefrom is missed.

On the other hand, a technique in which a cell culture substrate containing a polymer (A) of a (meth)acrylic acid ester monomer (a), an inorganic material (C), and a polymer (B) having a lower critical solution temperature has excellent culturability with respect to various types of cells and properties for easily detaching the cultured cells by lowering the environmental temperature, and the culturability and the detachability can be easily controlled depending on the cell type was reported (for example, refer to PTL 4).

The polymer (B) having the lower critical solution temperature which is used in the above-described invention is a single polymer mainly containing poly-N-isopropyl acrylamide, and the lower critical solution temperature is also a single temperature, and thus it is not possible to freely change (control) the lower critical solution temperature.

CITATION LIST

Patent Literature

[PTL 1] JP-B-6-104061
[PTL 2] JP-A-5-192138
[PTL 3] JP-A-5-192130
[PTL 4] Japanese Patent No. 4430123

SUMMARY OF INVENTION

Technical Problem

An object of the present invention is to provide a cell culture substrate in which a polymer (B) having a lower critical solution temperature which is contained in the substrate is an uncrosslinked copolymer of a monomer (a) that becomes a hydrophobic polymer in homopolymerization, and a monomer (b, c, or d) that becomes a hydrophilic polymer in homopolymerization. The lower critical solution temperature of the obtained copolymer (B) can be controlled widely by the types and ratio of the two monomers, the types and ratio of the two monomers are properly changed in accordance with the types of the cultured cells, and thus it is possible to culture cells with more excellent cell adhesiveness and proliferation. Further, the change of hydrophobicity and hydrophilicity of the culture substrate surface is rapidly performed with respect to the environmental temperature, and thus it possible to easily and rapidly detach the cultured cells from the culture substrate surface and collect the cells without using protein hydrolase such as trypsin and without damage to the cells at the time of detaching and collecting the cultured cells.

In addition, the polymer (B) in the cell culture substrate of the present invention has a multi-point interaction with the inorganic material (C), and thus has radiation proof sterilization properties.

In addition, another object of the present invention is to provide a method for producing the cell culture substrate, the method is performed by using a simple device and a simple process in which the cell culture substrate is easily attached on the surface of the plastic container while the polymer (B) having the lower critical solution temperature contained in the substrate is not subjected to crosslinking and a method such as the irradiation of electron beams is not used, and the length and concentration of the polymer (B) can be easily adjusted depending on the types (adhesiveness) of the cultured cells.

Solution to Problem

The inventor of the present invention has conducted intensive studies in order to achieve the above-described objects, and has completed the present invention by finding that the cell culture substrate which contains a polymer (A) of a (meth)acrylic acid ester monomer (a), one or more types of inorganic materials (C) selected from a water-swellable clay mineral and silica, and a polymer (B) having a lower critical solution temperature and including a monomer (a) and a monomer (b, c, or d) has excellent culturability with respect to various types of cells, and properties for easily detaching the cultured cells by lowering the environmental temperature, and depending on the cell type, the culturability and the detachability can be easily controlled by adjusting the types and ratio of the monomers.

That is, the present invention provides a cell culture substrate including a polymer (A) of a monomer (a) represented by the following Formula (1); a polymer (B) having the lower critical solution temperature; and one or more types of inorganic materials (C) selected from a water-swellable clay mineral and silica, in which the mass ratio ((C)/(A)) of the polymer (A) and the inorganic material (C) is in a range of 0.01 to 3, in which the polymer (B) is a copolymer (B1) of the monomer (a) and a hydrophilic amide-based vinyl monomer (b), a copolymer (B2) of the monomer (a) and a monomer (c) represented by the following Formula (2), or a copolymer (B3) of the monomer (a) and a polyethylene glycol chain-containing monomer (d) represented by the following Formula (3), and in which the content rate of the polymer (B) is in a range of 0.1% by mass to 40% by mass with respect to the entire cell culture substrate.

[Chem. 1]

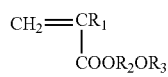
(1)

In the formula, $R_1$ is a hydrogen atom or a methyl group, $R_2$ represents an alkylene group having 2 to 3 carbon atoms, and $R_3$ represents an alkyl group having 1 to 2 carbon atoms.

[Chem. 2]

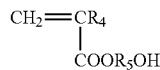
(2)

In the formula, $R_4$ represents a hydrogen atom or a methyl group, and $R_5$ represents an alkylene group having 2 to 3 carbon atoms.

[Chem. 3]

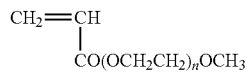
(3)

In the formula, n represents an integer of 2 to 20.

In addition, the present invention also provides a method for producing a cell culture substrate in which the hydrophilic amide-based vinyl monomer (b) is at least one type of monomer selected from the group consisting of an N-substituted (meth)acrylamide derivative, an N,N-disubstituted (meth) acrylamide derivative and N-vinylpyrrolidone, the method including a first step of producing a dispersion liquid (L) of a complex (X) of the polymer (A) and the inorganic material (C) by mixing the monomer (a), the inorganic material (C), and a polymerization initiator (D) into the aqueous medium (W) such that the concentration of the inorganic material (C) in the aqueous medium (W) is in a range defined by the following Expression (4) or Expression (5), and then polymerizing the monomers (a); and a second step of adding and mixing the polymer (B) into the dispersion liquid (L), and coating a support with the resulting mixture, followed by drying, in this order.

when Ra<0.19 is established, the concentration (% by mass) of the inorganic material (C)<12.4Ra+ 0.05 is satisfied.         Expression (4)

when Ra≥0.19 is established, the concentration (% by mass) of the inorganic material (c)<0.87Ra+ 2.17 is satisfied.         Expression (5)

In the expressions, the concentration (% by mass) of the inorganic material (C) is a numerical value obtained by dividing the mass of the inorganic material (C) by the total mass of the aqueous medium (W) and the inorganic material (C) and then multiplying the obtained value by 100, and Ra represents the mass ratio ((C)/(A)) of the inorganic material (C) and the polymer (A).

The most important feature of the cell culture substrate of the present invention is that a polymer (B) having a lower critical solution temperature is a copolymer of a monomer (a) that becomes a hydrophobic polymer in homopolymerization and a monomer (b, c, or d) that becomes a hydrophilic polymer in homopolymerization, and the lower critical solution temperature of the obtained copolymer (B) can be controlled widely by the types and ratio of the monomer, and depending on the cell type, it is possible to culture the cells with more excellent cell adhesiveness and proliferation by properly changing the types and ratio of the monomers. For example, the lower critical solution temperature of the polymer (B) which can be obtained at the same monomer ratio is differentiated depending on the types of monomers, and the monomer having high hydrophilicity and strong affinity to water causes the lower critical solution temperature to be on the higher temperature side. In addition, with respect to the monomer (a), as the ratio of the monomer (b, c, or d) is increased, the lower critical solution temperature of the obtained polymer (B) is shifted to the high temperature side, and the ratio and the lower critical solution temperature are in an almost linear relationship. The temperature for the cell culture is typically 37° C., and thus the types of the monomers and the copolymerization ratio are adjusted such that the lower critical solution temperature of the polymer (B) of the present invention is in the vicinity of 20 to 32° C.

In addition, the monomer (a) of the present invention is water-soluble, whereas the polymer (A) is hydrophobic and thus is not dissolved in water. Further, basically, in the cell culture substrate of the present invention, a part constituting the polymer (A) and the inorganic material (C) mainly has a function of attaching and proliferating cells, the polymer (B) having the lower critical solution temperature has a function of detaching the cells by changing the temperature, and each of these two parts can be independently controlled depending on the cell type. For example, at the time of culturing, the culturing temperature (37° C.) is higher than the lower critical solution temperature of the polymer (B), and thus the polymer (B) becomes a water-insoluble (hydrophobic) state, and the cells are attached and proliferated on the surface of the substrate; however, after the culturing of the cells is completed, when the temperature is lowered to equal to or lower than the lower critical solution temperature (for example, 10° C.), the polymer (B) becomes a water-soluble state, and thus extends to the aqueous solution (medium) from the substrate surface. With this, the cells are detached while being separated from the substrate surface.

The polymer (A) and the polymer (B) interact with the inorganic material (C) and thus the polymer (A) and the polymer (B), and the inorganic material (C) are bonded to each other mainly by an ionic bond and a hydrogen bond. At this time, the bonding force is strong and thus it is not possible to easily separate the polymer and the inorganic material (C) from each other. Due to the interaction therebetween, the polymers (A) and (B) are not easily cross-linked even in a case of being exposed to the radiation for sterilization (γ-ray or electron beam), and thus radiation proof sterilization properties are obtained.

The cell culture substrate of the present invention is formed of an inorganic material (C) and a thin layer of a complex (X) in which a polymer (A) is in an almost uniform layered structure, and a polymer (B) which extends toward the surface from the inside of the thin layer.

When the content of the polymer (B) is properly adjusted, the surface of the cell culture substrate is properly exposed without being completely covered with the polymer (B), and thus it is possible to maintain excellent cell adhesiveness and proliferation, and the cell detachability.

Advantageous Effects of Invention

In the cell culture substrate of the present invention, the hydrophobicity and the hydrophilicity are rapidly changed with respect to the environmental temperature, and depending on the types (adhesiveness) of the cultured cells, it is possible to easily control the types, the ratio, and the content of the monomers which form the polymer (B) having the lower critical solution temperature, and it is possible to rapidly detach the cultured cells from the culture substrate surface without using chemicals (such as trypsin), and collect the detached cells.

In addition, the production method for the present invention is performed by using a simple production device and a simple process in which a cell culture substrate is easily attached on a support (such as the plastic culture container) without using a polymerization method such as radiation of electron beams while a polymer (B) having the lower critical solution temperature contained in the substrate is not subjected to crosslinking (it is possible to maintain more rapid temperature responsiveness), and depending on the types (adhesiveness) of the cultured cells, the composition and content (concentration) of the polymer (B) can also be easily adjusted.

DESCRIPTION OF EMBODIMENT

A monomer (a) used in the invention can be preferably used as long as a polymer thereof reacts with an inorganic material (C) so as to form a complex by polymerizing an organic material and an inorganic material (for example, diacetone acrylamide can be used); however, a monomer (a) represented by the following Formula (1) is preferably used.

[Chem. 4]

In the formula, $R_1$ represents a hydrogen atom or a methyl group, $R_2$ represents an alkylene group having 2 to 3 carbon atoms, and $R_3$ represents an alkyl group having 1 to 2 carbon atoms.

With the monomer (a) used, it is possible to easily adjust the initial adhesiveness of cells, and thus a cell culture substrate having excellent cell proliferation and detachability can be obtained. In addition, in a case where the cell culture substrate is stacked on a surface of a support made of plastic such as polystyrene, it is possible to simply produce the cell culture substrate with high adhesiveness between the cell culture substrate and the surface of the support.

The monomer (a) may be used in combination of one or more types in accordance with the required mechanical properties and surface properties, and the adhesiveness of the substrate. In addition, to the extent that the culturability and properties of the cell culture substrate are not affected, other copolymerizable monomers can be used as necessary. As the copolymerizable monomer, an acrylic monomer having an anionic group such as a sulfone group and a carboxyl group, an acrylic monomer having a cationic group such as a quaternary ammonium group, an acrylic monomer having an amphoteric ion group containing a quaternary ammonium group and a phosphoric acid group, an acrylic monomer having an amino acid residue containing a carboxyl group and an amino group, an acrylic monomer having a sugar residue, an acrylic monomer having a hydroxyl group, an acrylic monomer having polyethylene glycol and a polypropylene glycol chain, an amphiphilic acrylic monomer having both a hydrophilic chain such as polyethylene glycol and a hydrophobic group such as a nonylphenyl group, polyethylene glycol diacrylate, an N-substituted (meth)acrylamide derivative, an N,N-disubstituted (meth) acrylamide derivative, and N,N'-methylenebisacrylamide can be used in combination. Here, the acrylic monomer includes an acrylamide monomer.

An inorganic material (C) used in the invention is one or more types of inorganic materials selected from a water-swellable clay mineral and silica. Examples of the water-swellable clay mineral include a water-swellable clay mineral which is capable of causing delamination to provide layers, and a clay mineral which is water-swellable, and uniformly dispersed in water or a solution obtained by water and an organic solvent is preferable, and an inorganic clay mineral which can be uniformly dispersed in a molecular shape (a single layer) or a similar shape of the molecular shape in water is particularly preferable. Specific examples thereof include water-swellable hectorite, water-swellable montmorillonite, water-swellable saponite, and water-swellable synthetic mica, which contain sodium as an interlayer ion. These clay minerals may be used in combination.

Examples of silica ($SiO_2$) used in the invention include colloidal silica. Among these, colloidal silica which can be uniformly dispersed in an aqueous solution, and has the particle size in a range of 10 nm to 500 nm is preferable, and colloidal silica having the particle size in a range of 10 to 50 nm is particularly preferable.

In the cell culture substrate of the present invention, the mass ratio of ((C)/(A)) of a polymer (A) to an inorganic material (C) is preferably in a range of 0.01 to 3, is further preferably in a range of 0.03 to 1, and particularly preferably in a range of 0.05 to 0.5. It is preferred that the mass ratio of ((C)/(A)) is in the above range, since the particle size of the complex formed of the clay minerals or silica and the polymer (A) is uniform and high stability of the aqueous dispersion liquid can be exhibited, and the surface properties (for example, the degree of hydrophilicity and hydrophobicity and the culturing of the cells) of the obtained coated film and the physical properties of the coated film are excellent, thereby obtaining a uniform coated film. Also, the adhesiveness to the support is excellent and no brittleness is caused.

In addition, in the cell culture substrate of the present invention, the content rate of the polymer (B) is preferably in a range of 0.1% by mass to 40% by mass, is further preferably in a range of 1% to 30% by mass, and particularly preferably in a range of 5% to 25% by mass, with respect to the entire substrate. When the content rate of the polymer (B) is in the above range, the cell adhesiveness and proliferation of the culture substrate, and detachability thereof at the time of lowering the temperature are excellent, and the surface smoothness of the culture substrate is satisfactory. In addition, when the culture substrate is layered on the surface of the plastic substrate, the coating properties and the adhesiveness to substrate surface are preferably satisfactory.

If the polymer (B) having the lower critical solution temperature which is used in the present invention is a copolymer of a monomer that becomes a hydrophilic polymer in homopolymerization, and a monomer that becomes a hydrophobic polymer in homopolymerization, and is capable of being transitioned to be a hydrophilic/hydrophobic state due to the temperature change, it can be preferably used; however, particularly, a copolymer (B1) of the monomer (a) and the hydrophilic amide-based vinyl monomer (b), a copolymer (B2) of the monomer (a) and the monomer (c) represented by the following Formula (2), or a copolymer (B3) of the monomer (a) and a polyethylene glycol chain-containing monomer (d) represented by the following Formula (3) are preferably used. The amide-based vinyl monomer (b) is preferably at least one type of monomer selected from the group consisting of an N-substituted (meth)acrylamide derivative such as N-methoxymethyl (meth)acrylamide, an N,N-disubstituted (meth)acrylamide derivative such as N,N-dimethyl (meth)acrylamide and (meth)acryloylmorpholine, and N-vinylpyrrolidone.

In addition, as the monomer (c), a monomer represented by the following Formula (2) is preferably used.

[Chem. 5]

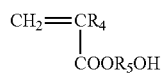
(2)

In the formula, $R_4$ represents a hydrogen atom or a methyl group, and $R_5$ represents an alkylene group having 2 to 3 carbon atoms.

Further, as the monomer (d), a monomer represented by the following Formula (3) is preferably used.

[Chem. 6]

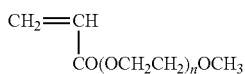
(3)

In the formula, n represents an integer of 2 to 20.

With these copolymers (B1, B2, or B3) being used, there is an advantage in that the lower critical solution temperature of the obtained copolymer (B) can be controlled widely by the types and ratio of the two monomers, the types and ratio of the two monomers are properly changed in accordance with the types of the cultured cells, and thus it is possible to culture cells with excellent cell adhesiveness and proliferation. Further, the change of hydrophobicity and hydrophilicity of the culture substrate surface is rapidly performed with respect to the environmental temperature, and thus it is possible to easily and rapidly detach the cultured cells from the culture substrate surface and collect the cells without using protein hydrolase such as trypsin, and without damage to the cells at the time of detaching and collecting the cultured cells. In addition, the polymer (B1, B2, or B3) preferably has strong interaction with the inorganic material (C), and the cell culture substrate itself is not easily detached in the culturing of the cells or in the operating of the detachment of cultured cells.

The above-described lower critical solution temperature has the properties that when a temperature is equal to or greater than the lower critical solution temperature, the polymer (B) becomes water-insoluble (hydrophobicity), and when a temperature is equal to or lower than the lower critical solution temperature, the polymer (B) becomes water-soluble (hydrophilicity). For example, regarding a copolymer of 2-methoxyethyl acrylate (monomer (a)) and N,N-dimethyl (meth)acrylamide (monomer (b)), the lower critical solution temperature is 15° C. when the ratio of the monomer (a) to the monomer (b) is 80:20 (molar ratio), and the lower critical solution temperature is 26° C. when the ratio of the monomer (a) to the monomer (b) is 70:30 (molar ratio), the lower critical solution temperature is 32° C. when the ratio of the monomer (a) to the monomer (b) is 64:36 (molar ratio), and the lower critical solution temperature is 37° C. when the ratio of the monomer (a) to the monomer (b) is 60:40 (molar ratio). With respect to the content (mol %) of N, N-dimethyl (meth) acrylamide (monomer (b)), when the lower critical solution temperature is plotted, an excellent linear relationship is exhibited (correlation coefficient $R^2$=0.9991).

Next, a production method for the present invention will be described.

A production method for the cell culture substrate includes a first step of producing a dispersion liquid (L) of a complex (X) of the polymer (A) and an inorganic material (C) by mixing the monomer (a), the inorganic material (C), and a polymerization initiator (D) into the aqueous medium (W), and then the monomers (a) are polymerized such that the concentration of the inorganic material (C) in an aqueous medium (W) is in a range defined by the following Expression (4) or Expression (5); and a second step of adding and uniformly mixing the polymer (B) into the dispersion liquid (L), and coating a support with the resulting mixture, followed by drying, in this order.

when Ra<0.19 is established, the concentration (% by mass) of the inorganic material (C)<12.4Ra+ 0.05 is satisfied.  Expression (4)

when Ra≥0.19 is established, the concentration (% by mass) of the inorganic material (C)<0.87Ra+ 2.17 is satisfied. Expression (5)

In the expressions, the concentration (% by mass) of the inorganic material (C) is a numerical value obtained by dividing the mass of the inorganic material (C) by the total mass of the aqueous medium (W) and the inorganic material (C) and then multiplying the obtained value by 100, and Ra represents the mass ratio ((C)/(A)) of the inorganic material (C) and the polymer (A).

The monomer (a), the inorganic material (C), and the polymer (B) which are used in the production method are the same as those which are described in the cell culture substrate, and therefore, the description thereof will be omitted.

The aqueous medium (W) which is used in the production method for the present invention is not particularly limited as long as the aqueous medium can include the monomer (a), the inorganic material (C), and the like, and an organic and inorganic complex dispersion liquid having excellent physical properties can be obtained through the polymerization. For example, the aqueous medium (W) may be an aqueous solution containing water, a solvent which is miscible with water and/or other compounds, and the aqueous solution may further contain a preservative and an antimicrobial agent, a coloring agent, perfumes, enzymes, proteins, collagen, sugars, peptides, amino acids, cells, DNA, salts, water-soluble organic solvents, a surfactant, a polymer compound, and a leveling agent.

As the polymerization initiator (D) which is used in the present invention, a well-known radical polymerization initiator can be used by being selected in a timely manner. A polymerization initiator having water-soluble properties or water dispersibility and capable of being uniformly contained in the entire system is preferably used. Specific examples of the polymerization initiator include water-soluble peroxides such as potassium peroxodisulfate and ammonium peroxodisulfate, a water-soluble azo compound such as VA-044, V-50, and V-501 (which are produced by Wako Pure Chemical Industries, Ltd.), and a mixture of $Fe^{2+}$ and hydrogen peroxide.

As the catalyst, N,N,N',N'-tetramethylethylenediamine and the like which are a tertiary amine compound can be preferably used. Here, a catalyst may not be necessarily used. The polymerizing temperature is may be selected in accordance with the kinds of the polymerizing catalysts and the initiators, for example, in a range of 0° C. to 100° C. The polymerizing time may be set to be in a range of several tens of seconds to several tens of hours.

On the other hand, a photopolymerization initiator is not easily affected by the oxygen inhibition, and the polymerization rate is fast, and thus is preferably used as the polymerization initiator (D). Specific examples thereof include acetophenones such as p-tert-butyl trichloro acetophenone, benzophenones such as 4,4'-bis-dimethyl-amino-benzophenone, ketones such as 2-methyl thioxanthone, benzoin ethers such as benzoin methyl ether, α-hydroxy ketones such as hydroxycyclohexyl phenyl ketone, phenylglyoxylates such as methyl benzoyl formate, and metallocenes.

The above-described photopolymerization initiator is water-insoluble. Here, "water-insoluble" means that the amount of polymerization initiator which is dissolved in water is equal to or less than 0.5% by mass. When the water-insoluble polymerization initiator is preferably used, it is likely that the initiators exist more in the vicinity of the clay minerals, and thus the start reaction point from the vicinity of the clay minerals becomes larger, the particle size distribution of the complex (X) of the obtained polymer (A) and the inorganic material (C) becomes narrower, and thus the dispersion liquid (L) becomes preferably highly stable.

It is preferable that a solution obtained by dissolving the photopolymerization initiator in a solvent (E) compatible with the aqueous medium (W) is added into the aqueous medium (W). With this method being used, the photopolymerization initiator can be more uniformly dispersed, and thereby it is possible to obtain the complex (X) having a more uniformed particle size.

The mass ratio of (D)/(E) of a photopolymerization initiator (D) and the solvent (E) in the solution in which the photopolymerization initiator (D) is dissolved in the solvent (E) is preferably in a range of 0.001 to 0.1, and is further preferably in a range of 0.01 to 0.05. If the range is equal to or greater than 0.001, it is possible to sufficiently provide the generation amount of radicals by irradiation of ultraviolet rays, thereby proceeding the polymerization reaction desirably, and if the range is equal to or lower than 0.1, coloring or odor does not substantially caused by the initiator, and the cost reduction is realized.

As the solvent (E) of the present invention, a solvent which can dissolve the photopolymerization initiator (D) and a water-insoluble polymerization initiator (D), and has a certain degree of water solubility can be used. Here, the solvent having the water solubility is preferably a solvent which can dissolve 50 g or more thereof with respect to 100 g of water. It is preferred that the solubility with respect to the water is equal to or greater than 50 g, since the dispersion properties of the water-insoluble polymerization initiator (D) with respect to the aqueous medium (W) are satisfactory, and the particle size of the obtained complex (X) is likely to be uniformed, thereby exhibiting the high stability of the dispersion liquid (L).

For example, examples of the water-soluble solvent include amides such as dimethylacetamide and dimethyl formamide, alcohols such as methanol, ethanol, and 2-propanol, dimethyl sulfoxide, and tetrahydrofuran. These solvents may be used in combination.

The addition amount of the solution obtained by dissolving the photopolymerization initiator (D) in the solvent (E) is preferably in a range of 0.1% by mass to 5% by mass, and is further preferably in a range of 0.2% by mass to 2% by mass, with respect to the total mass of the monomer (a), the inorganic material (C), the aqueous medium (W), the polymerization initiator (D), and the solvent (E). If the dispersion amount is equal to or greater than 0.1% by mass, it is enough to initiate the polymerization, and if it is equal to or less than 5% by mass, it is possible to reduce problems that the odor is generated due to the increase in the polymerization initiator in the complex (X) and the dispersed photopolymerization initiators are aggregated again, thereby obtaining the uniform dispersion liquid (L) of the complex (X).

The concentration (% by mass) of the inorganic material (C) with respect to the aqueous medium is in the range defined by Expression (4) or Expression (5), which is the feature of the method for producing the cell culture substrate of the present invention. It is preferred that the concentration (% by mass) of the inorganic material (C) with respect to the aqueous medium is in the range, since an excellent dispersion liquid (L) of the complex (X) can be obtained, the support can be easily coated with the dispersion liquid (L), and thereby a smooth and uniform, thin coated film can be obtained.

The dispersion liquid (L) produced by using the production method for the present invention may be used as it is, or may be used after a purifying step such as washing with water. In addition, a leveling agent, a surfactant, peptide, protein, collagen, amino acids, peptides, polysaccharides, a polymer compound or the like may be added in the dispersion liquid (L) for use.

Examples of the light for polymerization to be used in the first step of the present production method include electron beams, γ-rays, X-rays, ultraviolet rays, and visible light; however, among them, the ultraviolet rays are preferably used in terms of the simplicity of the device and handling. The intensity of the irradiation of the ultraviolet rays is preferably in a range of 10 to 500 mW/cm$^2$, and the irradiation time is typically in a range of about 0.1 seconds to 200 seconds. In the typical radical polymerization by heat, oxygen acts as an inhibitor of polymerization; however, in the present invention, the preparation of the solution and the polymerization by irradiation of ultraviolet rays are not necessary to be performed under an atmosphere in which oxygen is blocked, but can be performed under an air atmosphere. However, there are some cases where the irradiation of the ultraviolet rays is preferably performed under an inert gas atmosphere, since the polymerization rate can be further increased.

The coating method which is used in the second step of the present invention may be a conventionally used known method, for example, a casting method for casting the dispersion liquid to the support, a coating method performed by using a bar coater or a spin coater, or a spray method performed by spraying a solution. In addition, in a case where the coating is performed in a pattern shape, a method in which a patterned rubber plate is coated with the dispersion liquid and then the dispersion liquid is transferred to the support, a method in which a part of the support which is not to be coated is shielded in advance, and then the shielded part is removed, and a coating method by using an ink jet printer system can be used, for example.

The drying method is also not limited as long as a volatile component in the dispersion liquid (L) is volatilized such that a thin film of the complex (X) can be formed. For example, examples thereof include natural drying at room temperature, drying by wind at room temperature, heat or hot air, and far-infrared drying. Alternatively, a method for heating the dispersion liquid with hot air while rotating the dispersion liquid by using the spin coater can be used.

The weight-average molecular weight Mw of the polymer (B) in the production method is preferably in a range of $1\times10^4$ to $2\times10^7$, and is further preferably in a range of $1\times10^5$ to $5\times10^6$. If it is equal to or greater than $1\times10^4$, it is possible to maintain sufficient cell detachability, and if it is equal to or lower than $2\times10^7$, it is possible to maintain sufficient cell proliferation, and thereby it is possible to produce the cell culture substrate having high performance.

In the present production method, it is possible to widely adjust the rate of cell proliferation by adjusting the ratio of the monomer (a) to the inorganic material (C), and when the type of the polymer (B), the lower critical solution temperature, and the content rate are adjusted, it is possible to control the detaching rate of the cells by changing the temperature.

The surface of the cell culture substrate which is obtained by the present production method has a structure in which the entire surface is not covered with a single layer of the polymer (B), and the polymer (B) extends from the thin layer of the complex (X) such that the surface of the thin film is also properly exposed. The polymer (B) has a stable structure in which the polymer (B) is bonded to clay minerals or silica through an ionic bond and a hydrogen bond from the inside of the thin film of the complex (X) to the surface thereof, without being debonded due to the physical force and in water.

The shape of the cell culture substrate which is obtained by the present production method is not particularly limited as long as the cell culture can be performed and the cultured cells can be easily detached by the low temperature treatment. For example, examples of the shape include a dish shape, a bottle (bottle) shape, a tube shape, a bag (bag) shape, a multi-well plate shape, a micro-channel shape, a porous membrane or mesh shape (for example, a transwell and cell strainer), and a spherical shape in which the particle size thereof is preferably in a range of 10 to 500 μm, and further preferably in a range of 100 to 300 μm.

The material of the support which is obtained by the present production method is not particularly limited as long as the culture substrate can be sufficiently attached to the support, the cell culture can be performed on the attached culture substrate, and the cultured cells can be easily detached by the low temperature treatment. For example, a styrene-based resin such as polystyrene, a polyolefin-based resin such as polypropylene, a polyurethane-based resin, polycarbonate, polyethylene terephthalate (PET), a polysulfone-based resin, a fluorine-based resin, a polysaccharide natural polymer such as cellulose, an inorganic material such as glass and ceramics, or a metallic material such as stainless steel and titanium can be preferably used.

Further, the cell culture substrate of the present invention is surely used by being integrated with the support, and may be used alone by being detached from the support.

EXAMPLES

Hereinafter, the present invention will be specifically described with reference to Examples; however, the scope of the present invention is not limited thereto.

Reference Example

This reference example is an example in which a polymer (B1, B2, or B3) is synthesized and the lower critical solution temperature is measured.

A reaction solution (0) was prepared in such a manner that 2-methoxy-ethyl acrylate (monomer (a), produced by Toagosei Co., Ltd.), a monomer (b) (produced by Kohjin Co., Ltd.) or (c) (produced by Wako Pure Chemical Industries, Ltd.), or (d) (produced by Shin-Nakamura Chemical Industry Co., Ltd.) in the amount (unit: g) thereof indicated in Table 1, 24 μL of N,N,N',N'-tetramethylethylenediamine (produced by Wako Pure Chemical Industries, Ltd.) as a catalyst, 300 μL of 2% by weight potassium peroxodisulfate (produced by Wako Pure Chemical Industries, Ltd.) aqueous solution as a thermal polymerization initiator, and 30 g of water as an aqueous medium (W) were put into a glass container, and were uniformly mixed with each other while being nitrogen-substituted, and then the glass container was sealed.

[Preparation of Polymer (B) Aqueous Solution]

The aqueous solution of the polymer (B) was prepared in such a manner that the above-described reaction solution (0) was left to stand for 15 hours in a constant-temperature water bath at 20° C. The lower critical solution temperature (LCST) of the polymer (B) was obtained such a manner that the polymer (B) aqueous solution was put into a glass cell having the size of 10 mm×10 mm×45 mm (height), and then the change of light transmittance (light wavelength: 600 nm) of the aqueous solution within a temperature range of 10° C.

to 60° C. (the aqueous solution was transparent at a temperature which was equal to or lower than the LCST, and the aqueous solution was cloudy at a temperature which was equal to or higher than the LCST; here, a temperature at the midpoint of the transparency and cloudiness was set to the LCST) was measuring by using an ultraviolet visible spectrophotometer V-530 (produced by JASCO Co., Ltd.). The results are indicated in Table 2. According to the result in Table 2, it can be understood that the LCST of the obtained polymer (B) has an excellent linear relation with a component composition (a monomer (b, c, or d)). That is, reversely, the LCST of the obtained copolymer B can be easily estimated from the component composition.

Next, a monomer composition of each of the reaction solutions will be described.

TABLE 1

| Monomer (content of b, c, or d) (mol %) | MEA(a)/DMAA(b) | MEA(a)/ACMO(b) | MEA(a)/NVP(b) | MEA(a)/HEA(c) | MEA(a)/AM30G(d) |
|---|---|---|---|---|---|
| 20 | 0.6247 g/0.1188 g | 0.6247 g/0.1692 g | 0.6247 g/0.1332 g | — | 0.6247g/0.2616 g |
| 25 | — | 0.5856 g/0.2115 g | 0.5856 g/0.1665 g | — | — |
| 30 | 0.5466 g/0.1782 g | 0.5466 g/0.2538 g | 0.5466 g/0.1998 g | — | 0.5466 g/0.3924 g |
| 36 | 0.4998 g/0.2138 g | — | — | — | — |
| 40 | 0.4685 g/0.2376 g | 0.4658 g/0.3384 g | — | 0.4685 g/0.2784 g | 0.4685 g/0.5232 g |
| 50 | — | — | — | 0.3904 g/0.3480 g | — |
| 60 | — | — | — | 0.3123 g/0.4176 g | 0.3123 g/0.7848 g |

MEA: 2-methoxy-ethyl acrylate,
DMAA: N,N-dimethyl acrylamide,
ACMO: acryloylmorpholine,
NVP: N-vinylpyrrolidone,
HEA: 2-hydroxyethyl acrylate,
AM30G: methoxy triethylene glycol acrylate Next, the lower critical solution temperature of the polymer (B) in each composition will be described.

TABLE 2

| Monomer (content of | Lower critical solution temperature of polymer (B) (LCST) (° C.) | | | | |
|---|---|---|---|---|---|
| b, c, or d) (mol %) | MEA(a)/ DMAA(b) | MEA(a)/ ACMO(b) | MEA(a)/ NVP(b) | MEA(a)/ HEA(c) | MEA(a)/ AM30G(d) |
| 20 | (B1-1)15 | (B1-5)1 | (B1-9)10 | — | (B3-1)15 |
| 25 | — | (B1-6)9 | (B1-10)21 | — | — |
| 30 | (B1-2)26 | (B1-7)15 | (B1-11)41 | — | (B3-2)23 |
| 36 | (B1-3)29 | — | — | — | — |
| 40 | (B1-4)37 | (B1-8)26 | — | (B2-1)10 | (B3-3)31 |
| 50 | — | — | — | (B2-2)16 | — |
| 60 | — | — | — | (B2-3)23 | (B3-4)43 |
| Linear correlation coefficient ($R^2$) between LCST and content of monomer (b, c, or d) | 0.9991 | 0.9933 | 0.9899 | 0.9980 | 0.9936 |

Example 1

This example is an example of production of a cell culture substrate by using a polymer (B1).

[Preparation of Reaction Solution Containing Monomer (a), Inorganic Material (C), and Aqueous Medium (W)]

A reaction solution (1) was prepared by uniformly mixing 0.3254 g of 2-methoxy-ethyl acrylate (produced by Toagosei Co., Ltd.) as a monomer (a), 0.02 g of a water-swellable clay mineral, Laponite XLG (water-swellable hectorite, produced by Rockwood Additives Ltd.) as an inorganic material (C), and 10 g of water as an aqueous medium (W).

[Preparation of Solution in which Polymerization Initiator (D) is Dissolved in Solvent (E)]

A solution (DE) was prepared by uniformly mixing 9.8 g of methanol as a solvent (E), and 0.2 g of 1-hydroxy cyclohexyl phenyl ketone "Irgacure 184" (produced by Ciba-Geigy Corporation) as a polymerization initiator (D).

[Preparation of Dispersion Liquid (L) of Complex (X) (First Step)]

A dispersion liquid (L1) of a complex (X) having a pale milky-white color was prepared in such a manner that 50 μL of the solution (DE) was put into the entire amount of the reaction solution (1), was uniformly dispersed, and then was irradiated with ultraviolet rays having the intensity of 40 mW/cm² in a wavelength of 365 nm for 180 seconds.

In this reaction system, Ra=0.061, and the expression of the concentration (% by mass) of the inorganic material (C)=0.20(%)<12.4Ra+0.05=0.81 is satisfied.

[Production of Cell Culture Substrate (Second Step)]

3.0172 g of polymer (B1-3) aqueous solution (the polymer concentration=2.32% by weight) of "MEA (a)/DMAA (b) (the content of (b)=36 mol % and LCST=29° C., refer to Table 2)" which was obtained in the above-described reference example, and 150 μL of 20% by weight sodium dodecyl benzenesulfonate aqueous solution were put into the entire amount of the dispersion liquid (L1), were uniformly mixed with each other, and were put into a polystyrene culture dish (Treated Cell Culture Dish, product No. 430165, produced by Corning Incorporated) of 35 mm, and thereafter, the surface of the dish was thinly coated with the obtained mixture by using a spin coater, and was dried in a hot-air drier at 80° C. for 30 minutes. Subsequently, the dish was washed with sterile water, and then the dish was dried at 40° C. for five hours in a sterile bag, thereby obtaining a cell culture substrate 1.

The mass ratio of ((C)/(A)) of polymer (A) to the inorganic material (C) in the cell culture substrate 1 was 0.061, and the content rate of the polymer (B) was 16.9% by mass with respect to the entire cell culture substrate.

[Cell Culture and Test of Detachment and Collection by Temperature Change]

The proper amount of Ham'S F-12 culture media (produced by Wako Pure Chemical Industries, Ltd.) containing 10% serum was put into the obtained cell culture substrate 1, CHO-K1 cells (Chinese hamster ovary cell line) were seeded (seeding concentration: $2 \times 10^5$ per dish), and then the culturing was performed in 5% carbon dioxide at 37° C. for three days. Then, the culture medium (37° C.) was sucked, and a PBS aqueous solution (a phosphate buffer) having a temperature of 4° C. was added thereto, followed by being left to stand for about 10 minutes. Thereafter, a pipetting operation of sucking in and out the culture medium with a pipette was performed several times. Through the pipetting operation, it was found that most of the cells were detached from the surface of the culture substrate 1. The number of cells was measured by collecting naturally detached cells and then adding Reagent A and Reagent B (produced by chemometec) thereto, with a NucleoCounter produced by chemometec. Further, the number of remaining cells which were not detached was also measured by adding the Reagent A and the Reagent B to the culture substrate 1 after collecting the cells, with the NucleoCounter. The number of cells which were naturally detached and collected through a low temperature treatment was $9.2 \times 10^5$ cells, and the number of remaining cells which were not detached was $1.5 \times 10^5$ cells. When a collecting rate of the cells through the low temperature treatment was obtained from the following Equation (6), the cell collecting rate was about 86%.

cell collecting rate (%)={the number of cells collected through the low temperature treatment/ (the number of cells collected through the low temperature treatment+the number of the remaining cells which were not detached)}×100   Equation (6)

In addition, the total number of cells ($10.7 \times 10^5$ cells) which were collected from the above-described culture substrate 1 was about 0.99 times the number ($10.8 \times 10^5$ cells) in a case of using an uncoated dish (Treated Cell Culture Dish, product No. 430165, produced by Corning Incorporated), and the cell proliferation thereof was almost the same as that of the uncoated dish.

In addition, it was confirmed that the cells which were naturally detached through the above-described low temperature treatment and the remaining cells on the substrate which were not detached were in a normal cell state, by using a microscope.

From the example, it can be seen that the cell culture substrate containing the polymer (A), the temperature-responsive polymer (B), and the inorganic material (C) has both excellent culturability and a high collecting rate of the cells through the low temperature treatment.

Example 2

This example is also an example of production of a cell culture substrate by using a polymer (B1).

A cell culture substrate 2 was produced by using the same method as that in Example 1, except that 2.0408 g of polymer (B1-10) aqueous solution (polymer concentration=2.45% by weight) was used instead of 3.0172 g of polymer (B1-3) aqueous solution (polymer concentration=2.32% by weight) of the second step in Example 1.

The mass ratio of ((C)/(A)) of polymer (A) to the inorganic material (C) in the cell culture substrate 2 was 0.061, and the content rate of the polymer (B) was 12.6% by mass with respect to the entire cell culture substrate.

[Cell Culture and Test of Detachment and Collection by Temperature Change]

Cells were cultured in the same manner as in Example 1. The number of cells which were naturally detached through a cold PBS treatment was $13.1 \times 10^5$ cells and the number of remaining cells which were not detached was $1.0 \times 10^5$ cells. When a collecting rate of the cells through the low temperature treatment was obtained from. Equation (6), the cell collecting rate was about 93%.

In addition, the total number of cells ($14.1 \times 10^5$ cells) which were collected from the above-described culture substrate 2 was about 1.31 times the number ($10.8 \times 10^5$ cells) in a case of using an uncoated dish (Treated Cell Culture Dish, product No. 430165, produced by Corning Incorporated), and the cell proliferation thereof was greater than that of the uncoated dish.

In addition, it was confirmed that the cells which were naturally detached through the above-described low temperature treatment and the remaining cells on the substrate which were not detached were in a normal cell state, by using a microscope.

From the example, it can be seen that the cell culture substrate containing the polymer (A), the temperature-responsive polymer (B), and the inorganic material (C) has both excellent culturability and a high collecting rate of the cells through the low temperature treatment.

Example 3

This example is also an example of production of a cell culture substrate by using a polymer (B1).

[Preparation of Polymer (B1) Aqueous Solution]

0.7809 g of 2-methoxy-ethyl acrylate (monomer (a), produced by Toagosei Co., Ltd.), 0.1938 g of N-methoxymethyl methacrylamide (produced by Wako Pure Chemical Industries, Ltd.) as a monomer (b), 24 µL of N,N,N',N'-tetramethylethylenediamine (produced by Wako Pure Chemical Industries, Ltd.) as a catalyst, 300 µL of 2% by weight potassium peroxodisulfate (produced by Wako Pure Chemical Industries, Ltd.) aqueous solution as a thermal polymerization initiator, and 30 g of water as an aqueous medium (W) were put into a glass container, and were uniformly mixed with each other while being nitrogen-substituted, and then the glass container was sealed. Then, the aqueous solution of the polymer (B1) was prepared in such a manner that the above-described glass container was left to stand for 15 hours in a constant-temperature water bath at 20° C. The LCST of the polymer (B1) was 28° C.

[Production of Cell Culture Substrate (Second Step)]

A cell culture substrate 3 was produced by using the same method as that in Example 1, except that 3.1746 g of polymer (B1) aqueous solution (polymer concentration=3.15% by weight) was used instead of 3.0172 g of polymer (B1-3) aqueous solution (polymer concentration=2.32% by weight) of the second step in Example 1.

The mass ratio of ((C)/(A)) of polymer (A) to the inorganic material (C) in the cell culture substrate 3 was 0.061, and the content rate of the polymer (B) was 22.5% by mass with respect to the entire cell culture substrate.

[Cell Culture and Test of Detachment and Collection by Temperature Change]

Cells were cultured in the same manner as in Example 1. The number of cells which were naturally detached through a cold PBS treatment was $10.7 \times 10^5$ cells and the number of remaining cells which were not detached was $0.6 \times 10^5$ cells. When a collecting rate of the cells through the low temperature treatment was obtained from. Equation (6), the cell collecting rate was about 95%.

In addition, the total number of cells ($11.3 \times 10^5$ cells) which were collected from the above-described culture substrate 3 was about 1.05 times the number ($10.8 \times 10^5$ cells) in a case of using an uncoated dish (Treated Cell Culture Dish, product No. 430165, produced by Corning Incorporated), and the cell proliferation thereof was almost the same as that of the uncoated dish.

In addition, it was confirmed that the cells which were naturally detached through the above-described low temperature treatment and the remaining cells on the substrate which were not detached were in a normal cell state, by using a microscope.

From the example, it can be seen that the cell culture substrate containing the polymer (A), the temperature-responsive polymer (B), and the inorganic material (C) has both excellent culturability and a high collecting rate of the cells through the low temperature treatment.

Example 4

This example is an example of production of a cell culture substrate by using a polymer (B2).

[Preparation of Reaction Solution Containing Monomer (a), Inorganic Material (C), and Aqueous Medium (W)]

A reaction solution (4) was prepared by uniformly mixing 0.3604 g of 2-ethoxyethyl acrylate (produced by Sigma-Aldrich Japan K.K.) as a monomer (a), 0.08 g of a water-swellable clay mineral, Laponite XLG (produced by Rockwood Additives Ltd.) as an inorganic material (C), and 10 g of water as an aqueous medium (W).

[Preparation of Dispersion Liquid (L) of Complex (X) (First Step)]

A dispersion liquid (L4) of a complex (X) having a pale milky-white color was prepared in such a manner that 50 μL of the solution (DE) was put into the entire amount of the reaction solution (4), was uniformly dispersed, and then was irradiated with ultraviolet rays having the intensity of 40 mW/cm$^2$ in a wavelength of 365 nm for 180 seconds.

In this reaction system, Ra=0.22, and the expression of the concentration (% by mass) of the inorganic material (C)=0.79(%)<0.87Ra+2.17=2.36 is satisfied.

[Production of Cell Culture Substrate (Second Step)]

2.3729 g of polymer (B2-3) aqueous solution (the polymer concentration=2.95% by weight) of "MEA (a)/HEA (c) (the content of (c)=60 mol %, LCST=23° C., refer to Table 2)" which was obtained in the above-described reference example, and 150 μL of 20% by weight sodium dodecyl benzenesulfonate aqueous solution were put into the entire amount of the dispersion liquid (L4), were uniformly mixed with each other, and were put into a polystyrene culture dish (Treated Cell Culture Dish, product No. 430165, produced by Corning Incorporated) of 35 mm, and thereafter, the surface of the dish was thinly coated with the obtained mixture by using a spin coater, and was dried in a hot-air drier at 80° C. for 30 minutes. Subsequently, the dish was washed with sterile water, and then the dish was dried at 40° C. for five hours in a sterile bag, thereby obtaining a cell culture substrate 4.

The mass ratio of ((C)/(A)) of polymer (A) to the inorganic material (C) in the cell culture substrate 4 was 0.22, and the content rate of the polymer (B) was 13.7% by mass with respect to the entire cell culture substrate.

[Cell Culture and Test of Detachment and Collection by Temperature Change]

Cells were cultured in the same manner as in Example 1. The number of cells which were naturally detached through a cold PBS treatment was 11.6×10$^5$ cells and the number of remaining cells which were not detached was 0.2×10$^5$ cells. When a collecting rate of the cells through the low temperature treatment was obtained from. Equation (6), the cell collecting rate was about 98%.

In addition, the total number of cells (11.8×10$^5$ cells) which were collected from the above-described culture substrate 3 was about 1.09 times the number (10.8×10$^5$ cells) in a case of using an uncoated dish (Treated Cell Culture Dish, product No. 430165, produced by Corning Incorporated), and the cell proliferation thereof was almost the same as that of the uncoated dish.

In addition, it was confirmed that the cells which were naturally detached through the above-described low temperature treatment and the remaining cells on the substrate which were not detached were in a normal cell state, by using a microscope.

From the example, it can be seen that the cell culture substrate containing the polymer (A), the temperature-responsive polymer (B), and the inorganic material (C) has both excellent culturability and a high collecting rate of the cells through the low temperature treatment.

Example 5

This example is an example of production of a cell culture substrate by using a polymer (B3).

A cell culture substrate 5 was produced by using the same method as that in Example 1, except that the content of a water-swellable clay mineral, Laponite XLG as an inorganic material (C) was changed from 0.02 g" to 0.16 g and 1.3263 g of polymer (B3-2) aqueous solution (polymer concentration=3.77% by weight) was used instead of 3.0172 g of polymer (B1-3) aqueous solution of the second step in Example 1.

The mass ratio of ((C)/(A)) of polymer (A) to the inorganic material (C) in the cell culture substrate 5 was 0.49, and the content rate of the polymer (B) was 9.3% by mass with respect to the entire cell culture substrate.

In this reaction system, Ra=0.49, and the expression of the concentration (% by mass) of the inorganic material (C)=1.57(%)<0.87Ra+2.17=2.60 is satisfied.

[Cell Culture and Test of Detachment and Collection by Temperature Change]

Cells were cultured in the same manner as in Example 1. The number of cells which were naturally detached through a cold PBS treatment was 10.9×10$^5$ cells and the number of remaining cells which were not detached was 0.3×10$^5$ cells. When a collecting rate of the cells through the low temperature treatment was obtained from. Equation (6), the cell collecting rate was about 97%.

In addition, the total number of cells (11.2×10$^5$ cells) which were collected from the above-described culture substrate 5 was about 1.04 times the number (10.8×10$^5$ cells) in a case of using an uncoated dish (Treated Cell Culture Dish, product No. 430165, produced by Corning Incorporated), and the cell proliferation thereof was almost the same as that of the uncoated dish.

In addition, it was confirmed that the cells which were naturally detached through the above-described low temperature treatment and the remaining cells on the substrate which were not detached were in a normal cell state, by using a microscope.

From the example, it can be seen that the cell culture substrate containing the polymer (A), the temperature-responsive polymer (B), and the inorganic material (C) has both excellent culturability and a high collecting rate of the cells through the low temperature treatment.

Example 6

This example is also an example of production of a cell culture substrate by using a polymer (B3).

[Preparation of Polymer (B3) Aqueous Solution]

0.8784 g of 2-methoxy-ethyl acrylate (monomer (a), produced by Toagosei Co., Ltd.), 0.3615 g of methoxy polyethylene glycol 400 acrylate (product name: NKesterAM90G, produced by Shin-Nakamura Chemical Industry Co., Ltd.) as a monomer (d), 24 μL of N,N,N',N'-tetramethylethylenediamine (produced by Wako Pure Chemical Industries, Ltd.) as a catalyst, 300 μL of 2% by weight potassium peroxodisulfate (produced by Wako Pure Chemical Industries, Ltd.) aqueous solution as a thermal polymerization initiator, and 30 g of water as an aqueous medium (W) were put into a glass container, and were uniformly mixed with each other while being nitrogen-substituted, and then the glass container was sealed. Then, the aqueous solution of the polymer (B3) was prepared in such a manner that the above-described glass container was left to stand for 15 hours in a constant-temperature water bath at 20° C. The LCST of the polymer (B3) was 23° C.

[Production of Cell Culture Substrate (Second Step)]

A cell culture substrate 6 was produced by using the same method as that in Example 1, except that 1.2594 g of polymer (B3) aqueous solution (polymer concentration=3.97% by weight) was used instead of 3.0172 g of polymer (B1-3) aqueous solution (polymer concentration=2.32% by weight) of the second step in Example 1.

The mass ratio of ((C)/(A)) of polymer (A) to the inorganic material (C) in the cell culture substrate 6 was 0.061, and the content rate of the polymer (B) was 9.3% by mass with respect to the entire cell culture substrate.

[Cell Culture and Test of Detachment and Collection by Temperature Change]

Cells were cultured in the same manner as in Example 1. The number of cells which were naturally detached through a cold PBS treatment was $10.4 \times 10^5$ cells and the number of remaining cells which were not detached was $0.4 \times 10^5$ cells. When a collecting rate of the cells through the low temperature treatment was obtained from Equation (6), the cell collecting rate was about 96%.

In addition, the total number of cells ($10.8 \times 10^5$ cells) which were collected from the above-described culture substrate 6 was about 1.00 times the number ($10.8 \times 10^5$ cells) in a case of using an uncoated dish (Treated Cell Culture Dish, product No. 430165, produced by Corning Incorporated), and the cell proliferation thereof was almost the same as that of the uncoated dish.

In addition, it was confirmed that the cells which were naturally detached through the above-described low temperature treatment and the remaining cells on the substrate which were not detached were in a normal cell state, by using a microscope.

From the example, it can be seen that the cell culture substrate containing the polymer (A), the temperature-responsive polymer (B), and the inorganic material (C) has both excellent culturability and a high collecting rate of the cells through the low temperature treatment.

The results obtained from Examples 1 to 6 are indicated in the following Tables 3 and 4.

TABLE 3

| | Copolymer (B) | | | | | First step in production method | | | |
| --- | --- | --- | --- | --- | --- | --- | --- | --- | --- |
| | Monomer (a) | Monomer (b), (c), or (d) | Content rate with respect to entire cell culture substrate (% by mass) | LSCT (° C.) | (C)/(A) | Ra | 12.4Ra + 0.05 (Expression (4)) | 0.87Ra + 2.17 (Expression (5)) | Concentration (% by mass) of inorganic material (C) |
| Example 1 | MEA | DMAA(b) | 16.9 | 29 | 0.061 | 0.061 | 0.81 | — | 0.20 |
| Example 2 | MEA | NVP(b) | 12.6 | 21 | 0.061 | 0.061 | 0.81 | — | 0.20 |
| Example 3 | MEA | N-methoxymethyl methacrylamide (b) | 22.5 | 28 | 0.061 | 0.061 | 0.81 | — | 0.20 |
| Example 4 | MEA | HEA(c) | 13.7 | 23 | 0.22 | 0.22 | — | 2.39 | 0.79 |
| Example 5 | MEA | AM30G(d) | 9.3 | 23 | 0.49 | 0.49 | — | 2.60 | 1.57 |
| Example 6 | MEA | Methoxy polyethylene glycol 400 acrylate (d) | 9.3 | 23 | 0.061 | 0.061 | 0.81 | — | 0.20 |

TABLE 4

| | Number of seeding times | Number of cultured cells (total number) | Number of naturally detached cells | Number of cells which are not naturally detached | Collecting rate (%) | Cell proliferation* |
| --- | --- | --- | --- | --- | --- | --- |
| Example 1 | $2.0 \times 10^5$ | $10.7 \times 10^5$ | $9.2 \times 10^5$ | $1.5 \times 10^5$ | 86 | 0.99 |
| Example 2 | $2.0 \times 10^5$ | $14.1 \times 10^5$ | $13.1 \times 10^5$ | $1.0 \times 10^5$ | 93 | 1.31 |
| Example 3 | $2.0 \times 10^5$ | $11.3 \times 10^5$ | $10.7 \times 10^5$ | $0.6 \times 10^5$ | 95 | 1.05 |
| Example 4 | $2.0 \times 10^5$ | $11.8 \times 10^5$ | $11.6 \times 10^5$ | $0.2 \times 10^5$ | 98 | 1.09 |
| Example 5 | $2.0 \times 10^5$ | $11.2 \times 10^5$ | $10.9 \times 10^5$ | $0.3 \times 10^5$ | 97 | 1.04 |
| Example 6 | $2.0 \times 10^5$ | $10.8 \times 10^5$ | $10.4 \times 10^5$ | $0.4 \times 10^5$ | 96 | 1 |

*The ratio of uncoated dish to the number of cells

Example 7

This example is an example of the culturing of mesenchymal stem cells by using the culture substrates 1 to 6 which are produced in Examples 1 to 6, and a test of detachment and collection by temperature change.

[Cell Culture and Test of Detachment and Collection by Temperature Change]

The proper amount of MEM-α culture media (produced by Wako Pure Chemical Industries, Ltd.) containing 10% serum was put into the cell culture substrates 1 to 6 which were obtained in the above-described Examples 1 to 6, bone marrow-derived mesenchymal stem cells were seeded (seeding concentration: $1\times10^5$ per dish), and then the culturing was performed in 5% carbon dioxide at 37° C. for three days. Then, the culture medium (37° C.) was sucked, and a PBS aqueous solution (a phosphate buffer) having a temperature of 4° C. was added thereto, followed by being left to stand for about 10 minutes. Thereafter, a pipetting operation of sucking in and out the culture medium with a pipette was performed several times. Through the pipetting operation, it was found that most of the cells were detached from the surface of each of the culture substrates (1 to 6). The collecting rate of the cells which were naturally detached and the ratio (cell proliferation) of the number of cells which were naturally detached to the number of cells on the uncoated dish are indicated in Table 3.

TABLE 5

| Culture substrate | Polymer (B) having LCST | Number of seeding times | Number of cultured cells | Collecting rate of number of naturally detached cells (%) | Cell proliferation* |
|---|---|---|---|---|---|
| 1 | B1-3 (refer to Table 2) | $1.00 \times 10^5$ | $1.54 \times 10^5$ | 96.60 | 1.22 |
| 2 | B1-10 (refer to Table 2) | $1.00 \times 10^5$ | $1.64 \times 10^5$ | 96.90 | 1.30 |
| 3 | B1 | $1.00 \times 10^5$ | $1.34 \times 10^5$ | 96.24 | 1.06 |
| 4 | B2-3 (refer to Table 2) | $1.00 \times 10^5$ | $1.60 \times 10^5$ | 96.86 | 1.27 |
| 5 | B3-2 (refer to Table 2) | $1.00 \times 10^5$ | $1.60 \times 10^5$ | 96.33 | 1.27 |
| 6 | B3 | $1.00 \times 10^5$ | $1.34 \times 10^5$ | 96.20 | 1.06 |
| Uncoated dish | Treated Cell Culture Dish (430165, produced by Corning Inc.) | $1.00 \times 10^5$ | $1.26 \times 10^5$ | 21.83 | 1.00 |

*The ratio of uncoated dish to the number of cells

In addition, it was confirmed that the cells which were naturally detached through the above-described low temperature treatment and the remaining cells on the substrate which were not detached were in a normal cell state, by using a microscope.

From the example, it can be seen that the cell culture substrate containing the polymer (A), the temperature-responsive polymer (B), and the inorganic material (C) has both excellent culturability even with respect to stem cells and a high collecting rate of the cells through the low temperature treatment.

Example 8

This example is an example of culturing and collecting cells being in a thin film shape by using the culture substrate 1 produced in Example 1.

The proper amount of CS-C complete medium (produced by Cell Systems) was put into the culture substrate 1, normal human dermal fibroblasts were seeded (seeding concentration: $1.2\times10^4$ cell/cm$^2$), and then the culturing was performed in 5% carbon dioxide at 37° C. After confirming that the cells were sufficiently proliferated, the culture medium (37° C.) was sucked, and a PBS aqueous solution (a phosphate buffer) having a temperature of 4° C. was added thereto, followed by being left to stand for several minutes. Thus, the proliferated cells in the thin film shape were naturally detached.

In addition, it was confirmed that the cells in the thin film shape which were naturally detached through the above-described low temperature treatment were in a normal cell state, by using a microscope.

From the example, it can be seen that the cell culture substrate containing the polymer (A), the temperature-responsive polymer (B), and the inorganic material (C) has both excellent culturability and the thin film shaped cells are easily obtained through the low temperature treatment.

Example 9

This example is an example of production of a culturing bag by using a coating solution in Example 1.
[Production of Cell Culture Substrate (Second Step)]
3.0172 g of polymer (B1-3) aqueous solution which was obtained in the above-described reference example (refer to Table 2), and 150 µL of 20% by weight sodium dodecyl benzenesulfonate aqueous solution were put into the entire amount of the dispersion liquid (L1), and were uniformly mixed with each other. Subsequently, the proper amount of the mixture was put into the culturing bag (CultiLife 215, inner surface area: 215 cm$^2$, produced by Kohjin Bio Co., Ltd.) such that the entire inner surface was coated with the mixture, then the remaining solution was sufficiently removed, and then the inner surface was dried in the hot-air drier at 70° C. for 60 minutes. Then, after sufficiently washing the inside of the bag with sterile water, the dish was dried in the sterile bag at 40° C. for one night, and thereby a cell culture substrate (a culturing bag) 9 was obtained.
[Cell Culture and Test of Detachment and Collection by Temperature Change]

Cells were cultured in the same manner as in Example 1 (the cell seeding concentration is the same as that in Example 1 in terms of 35 mm of dish). The number of cells which were naturally detached through a cold PBS treatment was $13.1\times10^5$ cells/cm$^2$ and the number of remaining cells which were not detached was $0.04\times10^5$ cells/cm$^2$. When a collecting rate of the cells through the low temperature treatment was obtained from Equation (6), the cell collecting rate was about 97%.

In addition, the total number of cells ($1.34\times10^5$ cells/cm$^2$) which were collected from the above-described culture substrate 9 was about 0.99 times the number ($1.35\times10^5$ cells/cm$^2$) in a case of using an uncoated dish (Treated Cell Culture Dish, product No. 430165, surface area: 8 cm$^{2'}$ produced by Corning Incorporated), and the cell proliferation thereof was almost the same as that of the uncoated dish.

In addition, it was confirmed that the cells which were naturally detached through the above-described low temperature treatment and the remaining cells on the substrate which were not detached were in a normal cell state, by using a microscope.

From the example, it can be seen that the cell culture substrate (the culturing bag) containing the polymer (A), the temperature-responsive polymer (B), and the inorganic material (C) has both excellent culturability and a high collecting rate of the cells through the low temperature treatment.

Example 10

This example is also an example of production of a cell culture substrate by using silica as an inorganic material (C).

A cell culture substrate 10 was produced by using the same method as that in Example 1, except that 0.1 g of colloidal silica (product name: SNOWTEX 20 (20% by weight of silica concentration, produced by Nissan Chemical Industries, Ltd.)) was used instead of 0.02 g of a water-swellable clay mineral, Laponite XLG of Example 1.
[Cell Culture and Test of Detachment and Collection by Temperature Change]

Cells were cultured in the same manner as in Example 1. The number of cells which were naturally detached through a cold PBS treatment was $9.45 \times 10^5$ cells and the number of remaining cells which were not detached was $1.05 \times 10^5$ cells. When a collecting rate of the cells through the low temperature treatment was obtained from Equation (6), the cell collecting rate was about 90%. In addition, the total number of cells ($10.5 \times 10^5$ cells) which were collected from the above-described culture substrate 10 was about 0.97 times the number ($10.8 \times 10^5$ cells) in a case of using an uncoated dish (Treated Cell Culture Dish, product No. 430165, produced by Corning Incorporated), and the cell proliferation thereof was almost the same as that of the uncoated dish.

In addition, it was confirmed that the cells which were naturally detached through the above-described low temperature treatment and the remaining cells on the substrate which were not detached were in a normal cell state, by using a microscope.

From the example, it can be seen that the cell culture substrate containing the polymer (A), the temperature-responsive polymer (B), and silica (the inorganic material (C)) has both excellent culturability and a high collecting rate of the cells through the low temperature treatment.

Example 11

This example is an example of describing sterilization resistance of the cell culture substrate.

The cell culture substrate 6 produced in the preceding example was sterilized by electron beams with 10 kGy of irradiation amount (produced by Japan Irradiation Service Co., Ltd.). Next, cells were cultured in the same manner as in Example 1. The number of cells which were naturally detached through a cold PBS treatment was $10.69 \times 10^5$ cells and the number of remaining cells which were not detached was $0.33 \times 10^5$ cells. When a collecting rate of the cells through the low temperature treatment was obtained from Equation (6), the cell collecting rate was about 97%.

In addition, the total number of cells ($11.02 \times 10^5$ cells) which were collected from the above-described culture substrate 6 was about 1.02 times the number ($10.8 \times 10^5$ cells) in a case of using an uncoated dish (Treated Cell Culture Dish, product No. 430165, produced by Corning Incorporated), and the cell proliferation thereof was almost the same as that of the uncoated dish.

In addition, it was confirmed that the cells which were naturally detached through the above-described low temperature treatment and the remaining cells on the substrate which were not detached were in a normal cell state, by using a microscope.

From the example, it can be seen that with respect to the cell culture substrate containing the polymer (A), the temperature-responsive polymer (B), and the inorganic material (C), excellent culturability and a high collecting rate of the cells through the low temperature treatment are not changed, even if the sterilization was performed by radiation.

Example 12

This example is an example of production of culture micro carrier beads by using the coating solution in Example 1.
[Production of Cell Culture Substrate (Second Step)]

3.0172 g of polymer (B1-3) aqueous solution which was obtained in the above-described reference example (refer to Table 2), and 150 μL of 20% by weight sodium dodecyl benzenesulfonate aqueous solution were put into the entire amount of the dispersion liquid (L1) and were uniformly mixed with each other, thereby obtaining a coating solution.

A small amount of the polystyrene beads (product name: PolyBeads, produced by Poly Sciences Inc.) having an average particle size of 300 μm was put into a cell strainer (Cell Strainer, produced by BD Falcon) made of nylon mesh, which has 70 μm holes, and then the proper amount of coating solution which was prepared described above was added dropwise to the surface of beads so as to wet the surface of the beads with the coating solution. Then, the cell strainer was put into six well plates, the excess coating solution was removed from the surface of the beads by using a centrifuge under the condition of 2,000 rpm, and then the coated surface was dried in the hot-air drier at 70° C. for 30 minutes. Thereafter, the coated beads were sufficiently washed with sterile water at 50° C., thereby obtaining culture micro carrier beads 12.
[Cell Culture and Test of Detachment and Collection by Temperature Change]

The obtained culture micro carrier beads 12 was put into a 35 mm of dish (60 mm/Non-Treated Dish, produced by Asahi Techno Glass Co., Ltd.) made of polystyrene, and then the proper amount of Doulbecco's modified Eagle's Medium (DMEM) (10% of FBS is added) (produced by Nissui Pharmaceutical Co., Ltd.) was added thereinto. Then, Balb3T3 cells (murine tumor fibroblasts) were seeded (seeding concentration: $1.0 \times 10^4$ cell/cm$^2$), and then the culturing was performed in 5% carbon dioxide at 37° C. After four hours from the start of the culturing, it was confirmed that the cells were attached on the surface of the beads, by using a microscope. Further, in three days from the culturing, it was observed that almost the entire surface of the beads was covered with the cells. Subsequently, when the culture medium at 37° C. of the culture micro carrier beads after 3 days from the start of the culturing was replaced with the culture medium at 4° C., and then the culture medium at 4° C. was left to stand for several minutes, it was observed that a portion of the cells was detached from the surface of the beads. In addition, when the "pipetting" operation of sucking in and out the culture medium with a pipette was performed several times, it was observed that all of the cells on the surface of the beads were detached (the collecting rate of the detached cells were 100%).

In addition, it was confirmed that the cells which were detached through the above-described low temperature treatment and the pipetting operation were in a normal cell state, by using a microscope.

From the example, it can be seen that the cell culture substrate (culture micro carrier beads) containing the polymer (A), the temperature-responsive polymer (B), and the inorganic material (C) has both excellent culturability and a high collecting rate of the cells through the low temperature treatment and the pipetting operation.

Comparative Example 1

This comparative example is an example of the cell culture by using a commercially available cell culture dish and the natural detachment due to the low temperature treatment.

Cells were cultured in the same manner as in Example 1 except for using the commercially available cell culture dish (Treated Cell Culture Dish, product No. 430165, produced by Corning Incorporated). The number of cells which were naturally detached through a cold PBS treatment was $2.2 \times 10^5$ cells and the number of remaining cells which were not detached was $8.6 \times 10^5$ cells. When a collecting rate of the cells through the low temperature treatment was obtained from. Equation (6), the cell collecting rate was about 20%.

From the comparative example, it can be seen that as compared with the culture substrate of the present invention, the proliferation of the cell in the commercially available culture substrate is not changed; however, it is not likely that the cells are naturally detached by the low temperature treatment.

Comparative Example 2

This comparative example is an example of the cell culture substrate which does not contain the polymer (B).

A cell culture substrate 2' was produced in the same manner as in Example 5, except that polymer (B3-2) aqueous solution of the second step was not added in the production method of Example 5.

[Cell Culture and Test of Detachment and Collection by Temperature Change]

Cells were cultured in the same manner as in Example 1. The number of cells which were naturally detached through a cold PBS treatment was $0.99 \times 10^5$ cells and the number of remaining cells which were not detached was $10.01 \times 10^5$ cells. When a collecting rate of the cells through the low temperature treatment was obtained from. Equation (6), the cell collecting rate was about 9%.

In addition, the total number of cells ($11.0 \times 10^5$ cells) which were collected from the above-described culture substrate 5 was about 1.02 times the number ($10.8 \times 10^5$ cells) in a case of using an uncoated dish (Treated Cell Culture Dish, product No. 430165, produced by Corning Incorporated), and the cell proliferation thereof was almost the same as that of the uncoated dish.

From the comparative example, it can be seen that in a case where the polymer (B) is not contained, the proliferation of the cell is not changed while the cell collecting rate is greatly decreased.

Comparative Example 3

This comparative example is an example of the cell culture substrate which excessively contains the polymer (B).

[Production of Cell Culture Substrate (Second Step)]

A cell culture substrate 3' was produced by using the same method as that in Example 1, except that the amount of the polymer (B1-3) aqueous solution which was mixed into the entire amount of the dispersion liquid (L1) in Example 1 was changed from 3.0172 g to 10.3448 g.

The content rate of the polymer (B) was 41.0% by mass with respect to the entire cell culture substrate 3'.

[Cell Culture and Test of Detachment and Collection by Temperature Change]

Normal human dermal fibroblasts were cultured in the same manner as in Example 8. The cells were not attached onto the substrate and the seeded cells were dead, and thus it was not possible to find the proliferation.

From the comparative example, it can be seen that if the polymer (B) is excessively contained, the attachment and proliferation of the cells are inhibited, and thus the cell culture cannot be performed.

Comparative Example 4

This comparative example is an example of the cell culture by using commercially available polystyrene beads.

Balb3T3 cells were cultured in the same manner as in Example 12 except for using the commercially available polystyrene beads (product name: PolyBeads, produced by Poly Sciences Inc.). The cell aggregations were found in the culture medium, but any cell was not observed on the surface of the beads.

From the comparative example, it can be seen that the commercially available polystyrene beads do not have attachment and proliferation of the cells as compared with the culture micro carrier beads 12 of the present invention.

Comparative Example 5

This comparative example is an example of a case where the concentration of the inorganic material (C) was beyond the range defined by Expression (5).

[Preparation of Reaction Solution Containing Monomer (a), Water-Swellable Inorganic Material (C), and Aqueous Medium (W)]

1.32 g of 2-methoxyethyl acrylate (produced by Toagosei Co., Ltd.) as a monomer (a), 0.32 g of a water-swellable clay mineral, Laponite XLG (produced by Rockwood Additives Ltd.) as an inorganic material (C), 50 µL of solution (DE) as a polymerization initiator, and 10 g of water as an aqueous medium (W) were uniformly mixed with each other so as to prepare a reaction solution (4'). Next, when the reaction solution (4') was irradiated with ultraviolet rays having the intensity of 40 mW/cm$^2$ in a wavelength of 365 nm for 180 seconds, the entire reaction solution (4') was gelated. The obtained gel was in the gel state without being dissolved and dispersed even in a large amount of water.

In this reaction system, Ra=0.24, and the expression of the concentration (% by mass) of the inorganic material (C)=3.10%>0.87Ra+2.17=2.38 is satisfied.

From the comparative example, it can be seen that if the concentration (% by mass) of the inorganic material (C) is beyond the range defined in Expression (5), the entire reaction solution is gelated, and thus the dispersion liquid (L) of the complex (X) cannot be obtained, and thereby it is not possible to produce the cell culture substrate by performing the coating on the dish.

As apparently described in the above-described Examples and Comparative Examples, the cell culture substrate of the present invention has the excellent adhesiveness to the support formed of another material, and has a function of performing the excellent cell culture and naturally detaching the cells by the temperature change. In addition, it was obvious that the cell culture substrate could be easily produced in a short time.

INDUSTRIAL APPLICABILITY

The cell culture substrate of the present invention can be used in the preparation of colony-like cell groups or two-dimensional sheet-like cells, and three-dimensional cell proliferated matters in the fields of biochemistry, drug discovery and regenerative medicine.

The invention claimed is:

1. A cell culture substrate, comprising:
a polymer (A) of a monomer (a) represented by the following Formula (1);
a polymer (B) having a lower critical solution temperature; and
one or more inorganic materials (C) selected from a water-swellable clay mineral and silica,
wherein the mass ratio ((C)/(A)) of the polymer (A) and the inorganic material (C) is in a range of 0.01 to 3;
wherein the polymer (B) is a copolymer (B1) of the monomer (a) and a hydrophilic amide-based vinyl monomer (b), a copolymer (B2) of the monomer (a) and a monomer (c) represented by the following Formula (2), or a copolymer (B3) of the monomer (a) and a polyethylene glycol chain-containing monomer (d) represented by the following Formula (3); and
wherein the content rate of the polymer (B) is in a range of 0.1% by mass to 40% by mass with respect to the entire cell culture substrate,

[Chem. 1]

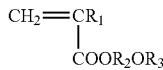     (1)

wherein $R_1$ represents a hydrogen atom or a methyl group, $R_2$ represents an alkylene group having 2 to 3 carbon atoms, and $R_3$ represents an alkyl group having 1 to 2 carbon atoms;

[Chem. 2]

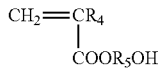     (2)

wherein $R_4$ represents a hydrogen atom or a methyl group, and $R_5$ represents an alkylene group having 2 to 3 carbon atoms; and

[Chem. 3]

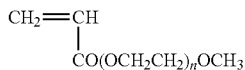     (3)

wherein n represents an integer of 2 to 20.

2. The cell culture substrate according to claim 1, wherein the hydrophilic amide-based vinyl monomer (b) is at least one monomer selected from the group consisting of an N-substituted (meth)acrylamide derivative, an N,N-disubstituted (meth)acrylamide derivative, and N-vinylpyrrolidone.

3. The cell culture substrate according to claim 2, wherein the water-swellable clay mineral is one or more clay minerals selected from water-swellable hectorite, water-swellable montmorillonite, water-swellable saponite, and water-swellable synthetic mica, which cause delamination in an aqueous medium (W) to provide 1 to 10 layers, and
wherein the silica is water dispersible colloidal silica.

4. A production method for the cell culture substrate according to claims 2, the method comprising:
a first step of producing a dispersion liquid (L) of a complex (X) of the polymer (A) and the inorganic material (C) by mixing the monomer (a), the inorganic material (C), and a polymerization initiator (D) into a aqueous medium (W) such that the concentration of the inorganic material (C) in the aqueous medium (W) is in a range defined by the following Expression (4) or Expression (5), and then polymerizing the monomers (a); and
a second step of adding and mixing the polymer (B) into the dispersion liquid (L), and coating a support with the resulting mixture, followed by drying, in this order, when Ra<0.19 is established, the concentration (% by mass) of the inorganic material (C)<12.4Ra+ 0.05 is satisfied; and     Expression (4)

when Ra≥0.19 is established, the concentration (% by mass) of the inorganic material (c)<0.87Ra+ 2.17 is satisfied     Expression (5), wherein the concentration (% by mass) of the inorganic material (C) is a numerical value obtained by dividing the mass of the inorganic material (C) by the total mass of the aqueous medium (W) and the inorganic material (C) and then multiplying the obtained value by 100, and Ra represents the mass ratio ((C)/(A)) of the inorganic material (C) and the polymer (A).

5. The cell culture substrate according to claim 1, wherein the water-swellable clay mineral is one or more clay minerals selected from water-swellable hectorite, water-swellable montmorillonite, water-swellable saponite, and water-swellable synthetic mica, which cause delamination in an aqueous medium (W) to provide 1 to 10 layers, and
wherein the silica is water dispersible colloidal silica.

6. A production method for the cell culture substrate according to claim 5, the method comprising:
a first step of producing a dispersion liquid (L) of a complex (X) of the polymer (A) and the inorganic material (C) by mixing the monomer (a), the inorganic material (C), and a polymerization initiator (D) into a aqueous medium (W) such that the concentration of the inorganic material (C) in the aqueous medium (W) is in a range defined by the following Expression (4) or Expression (5), and then polymerizing the monomers (a); and
a second step of adding and mixing the polymer (B) into the dispersion liquid (L), and coating a support with the resulting mixture, followed by drying, in this order, when Ra<0.19 is established, the concentration (% by mass) of the inorganic material (C)<12.4Ra+ 0.05 is satisfied; and     Expression (4);

when Ra≥0.19 is established, the concentration (% by mass) of the inorganic material (c)<0.87Ra+ 2.17 is satisfied     Expression (5):, wherein the concentration (% by mass) of the inorganic material (C) is a numerical value obtained by dividing the mass of the inorganic material (C) by the total mass of the aqueous medium (W) and the inorganic material (C) and then multiplying the obtained value by 100, and Ra represents the mass ratio ((C)/(A)) of the inorganic material (C) and the polymer (A).

7. A production method for the cell culture substrate according to claim 1, the method comprising:

a first step of producing a dispersion liquid (L) of a complex (X) of the polymer (A) and the inorganic material (C) by mixing the monomer (a), the inorganic material (C), and a polymerization initiator (D) into a aqueous medium (W) such that the concentration of the inorganic material (C) in the aqueous medium (W) is in a range defined by the following Expression (4) or Expression (5), and then polymerizing the monomers (a); and a second step of adding and mixing the polymer (B) into the dispersion liquid (L), and coating a support with the resulting mixture, followed by drying, in this order, when Ra<0.19 is established, the concentration (% by mass) of the inorganic material (C)<12.4Ra+ 0.05 is satisfied; and                    Expression (4);

when Ra ≥0.19 is established, the concentration (% by mass) of the inorganic material (c)<0.87Ra+ 2.17 is satisfied                    Expression (5), wherein the concentration (% by mass) of the inorganic material (C) is a numerical value obtained by dividing the mass of the inorganic material (C) by the total mass of the aqueous medium (W) and the inorganic material (C) and then multiplying the obtained value by 100, and Ra represents the mass ratio ((C)/(A)) of the inorganic material (C) and the polymer (A).

8. A production method for the cell culture substrate according to claim 3, the method comprising:

a first step of producing a dispersion liquid (L) of a complex (X) of the polymer (A) and the inorganic material (C) by mixing the monomer (a), the inorganic material (C), and a polymerization initiator (D) into a aqueous medium (W) such that the concentration of the inorganic material (C) in the aqueous medium (W) is in a range defined by the following Expression (4) or Expression (5), and then polymerizing the monomers (a); and a second step of adding and mixing the polymer (B) into the dispersion liquid (L), and coating a support with the resulting mixture, followed by drying, in this order, when Ra<0.19 is established, the concentration (% by mass) of the inorganic material (C)<12.4Ra+ 0.05 is satisfied; and                    Expression (4);

when Ra≥0.19 is established, the concentration (% by mass) of the inorganic material (c)<0.87Ra+ 2.17 is satisfied                    Expression (5), wherein the concentration (% by mass) of the inorganic material (C) is a numerical value obtained by dividing the mass of the inorganic material (C) by the total mass of the aqueous medium (W) and the inorganic material (C) and then multiplying the obtained value by 100, and Ra represents the mass ratio ((C)/(A)) of the inorganic material (C) and the polymer (A).

* * * * *